United States Patent [19]

Solomon

[11] Patent Number: 5,688,651
[45] Date of Patent: Nov. 18, 1997

[54] PREVENTION OF PROTEIN AGGREGATION

[75] Inventor: Beka Solomon, Herzlya, Israel

[73] Assignee: RAMOT University Authority For Applied Research and Development Ltd., Tel Aviv, Israel

[21] Appl. No.: 358,786

[22] Filed: Dec. 16, 1994

[51] Int. Cl.$^6$ .................... G01N 33/53; G01N 33/48; A61K 39/395; C07K 16/00
[52] U.S. Cl. .................... 435/7.1; 424/130.1; 436/63; 530/388.1
[58] Field of Search .................... 424/130.1, 135.1, 424/141.1; 435/7.1; 436/63; 514/44; 530/387.1, 388.1, 388.2, 389.1, 390.5

[56] References Cited

U.S. PATENT DOCUMENTS 4,946,778  8/1990  Ladner et al. .................... 435/69.6

FOREIGN PATENT DOCUMENTS

WO 93/11248  6/1993  WIPO.
9313200  7/1993  WIPO.
9311248  10/1993  WIPO.
9408012  4/1994  WIPO.
9411513  5/1994  WIPO.

OTHER PUBLICATIONS

Carlson et al, "Antibody assisted protein refolding" Bio/Technology, vol. 10, pp. 86–91, Jan. 1992.
Tomiyama et al, "Rifampicin prevents the aggregation of neurotoxicity of amyloid B protein in vitro", Biochem. and Biophys. Res. Comm., vol. 204, No. 1, pp. 76–83, Oct. 14, 1994.
Craig, E.A. "Caperones: Helpers along the pathways to protein folding" Science, vol. 260, pp. 1902–1903, Jun. 25, 1993.
Agard, D.A. "To fold or not to fold . . . " Science, vol. 260, pp. 1903–1904, Jun. 25, 1993.
Banks and Kastin, "Peptide binding in blood and passage across the blood–brain barrier" in *Blood Binding and Drug Transfer*, editors Tillement and Eckert, pp. 223–241, (1992).
Blond and Goldberg, "Partly native epitopes are already present on early intermediates in the folding of tryptophan synthase" *PNAS* (USA), 84:1147–1151 (1987).
Brems, "Solubility of different folding conformers of bovine growth hormone" *Biochemistry* 27:4541–4545 (1988).
Burdick et al., "Assembly and aggregation properties of synthetic Alzheimer's A4/β amyloid peptide analogs" *J. Biol Chem.* 267, 546–554 (1992).
Bush et al., "Rapid induction of alzheimer Aβ amyloid formation by zinc" *Science* 265:1465–1467 (1994).
Carlson and Yarmush, "Antibody assisted protein refolding" *Bio/Technology*, 10:86–91 (1992).
Chothia and Janin, "Principles of protein–protein recognition" *Nature* 256:705–708 (1975).
De Young et al., "Aggregation of globular proteins" *Accounts of Chemical Research*, 26:614–620 (1993).
Duenas et al., "Intra–and extracellular expression of an scFv antibody . . . " *BioTechniques*, 16:476–483 (1994).

Ellis and Van Der Viies, "Molecular chaperones" *Annu. Rev. Biochem.* 60:321–347 (1991).
Fraser et al., "Effects of sulfate ions on alzheimer β/A4 peptide assemblies . . . " *J. Neurochem.* 59:1531–1540 (1992).
Frederickson, *Int. Rev. Neuorobiol.* 31:145–238, (1989).
Gething and Sambrook, "Protein folding in the cell" *Nature* 355:33–45 (1992).
Goldberg, "Investigating protein conformation, dynamics and folding with monoclonal antibodies" *TIBS* 16:358–362 (1991).
Goloubinoff et al., "Reconstitution of active dimeric ribulose bisphosphate carboxylase . . . " *Nature*, 342:884–889 (1989).
Haass and Selkoe, "Cellular Processing of β–amyloid precursor protein and the genesis of amyloid β–peptide" *Cell*, 75:1039–1042 (1993).
Haber, "Engineered antibodies as pharmacological tools" *Immunological Reviews*, 130:189–212 (1992).
Harlow and Lane, in *Antibodies, a Laboratory Manual*, Chapter 6, Production of Monoclonal Antibodies, Cold Spring Harbor Laboratory, (1988).
Hattori et al., "Unfolding/refolding studies on bovine β–Lactoglobulin with monoclonal antibodies as probes" *J. Biol. Chem.* 268:22414–22419 (1993).
Hendrick and Hartl, "Molecular chaperone functions of heat–shock proteins" *Annu. Rev. Biochem,* 62:349–394 (1993).
Jaenicke, "Protein folding: local structures, domains, subunits, and assebmlies" *Biotechemistry*, 30:3147–3161 (1991).
Mantyh et al., "Aluminum, iron, and zinc ions promote aggregation of physiological concentrations . . . " *J. Neurochem.* 61:1171–1173 (1993).
Marasco et al., "Design, intracellular expression and activity of a human anti–human immunodeficiency . . . " *Proc. Natl. Acad. Sci. USA*, 90:7889–7893 (Aug., 1993).
McLachlan et al., "Intramuscular desferrioxamine in patients with Alzheimer's disease" *Lancet*, 337:1304–1308 (1991).
Milstein, "Monoclonal antibodies" *Scientific American*, pp. 56–64 (Oct., 1980).
Pluckthun, "Mono–and bivalent antibody fragments produced in *Escherichia coli*: engineering, folding and antigen binding" *Immunol. Reviews*, 130:151–188 (1992).

(List continued on next page.)

Primary Examiner—Lila Feisee
Assistant Examiner—Yvonne Eyler
Attorney, Agent, or Firm—Kohn & Associates

[57] ABSTRACT

A method of selecting anti-aggregation molecules with chaperone-like activity that have characteristics including binding to a native target molecule epitope with a high binding constant and are non-inhibitory to the biological activity of the target molecule. The method molecules denaturating a target molecule in the presence of presumptative antiaggregation molecules to prevent the target molecules from self-or induced-aggregation. The nonaggregated target molecule coupled to the anti-aggregation molecule is then tested for bioactivity.

4 Claims, 3 Drawing Sheets

OTHER PUBLICATIONS

Rao et al., "Chaperone–like activity of α–crystallin" *J. Biol. Chem.* 269:13266–13272 (1994).

Silen and Agard, "The α–lytic protease pro–region does not require a physical linkage to activate . . . " *Nature,* 341:462–464 (1989).

Solomon et al., "Interaction of carboxypeptidase with a monoclonal antibodies" *Molec. Immunol.,* 21:1–12 (1984).

Solomon et al., "Localization of a highly immunogenic region of Carboxypeptidase A . . . " *Biochemistry,* 28:1235–1241 (1989).

Solomon and Balas, "Thermostabilization of Carboxypeptidase A by interaction with its monoclonal antibodies" *Biotechnol. Appl. Biochem.,* 14:202–211 (1991).

Solomon and Schwartz, "Chaperone–like effect of monoclonal antibodies on refolding of heat denatured Carboxypeptidase A" *J.Molec.Recog.* (in press), (1995).

Stern et al., "Antibodies to the β–amyloid peptide cross–react with conformational epitopes in human fibrinogen . . . " *FEBS Lett.* 264:43–47, (1990).

Talafous et al., "Solution structure of residues 1–28 of the amyloid β–peptide" *Biochemistry,* 33:7788–7796 (1994).

Travis, "Putting antibodies to work inside cells" *Science,* 261:1114 (1993).

Tuomanen et al., "Reversible opening of the blood–brain barrier by anti–bacterial antibodies" *Proc. Natl. Acad. Sci. USA,* 90:7824–7828 (Aug., 1993).

Vallee and Riordan, *Ann. Rev. Biochem.* 38:733–794 (1969).

Vallee and Galdes, *Advances in Enzymology and Related Areas of Molecular Biology,* 56:282–430, (1984).

Vandenbroeck et al., "Refolding and single–step purification of porcine interferon–γ . . . " *Eur. J. Biochem.,* 215;481–486 (1993).

Welch, "How cells respond to stress" *Scientific American,* pp. 56–64 (May, 1993).

Wetzel, "Mutations and off–pathway aggregation of proteins" *TIBTECH,* 12:193–198 (1994).

Wetzel et al., *Bio/Technol.,* 9:731–737 (1991).

Winther et al., "Refolding of a carboxypeptidase Y folding intermediate in vitro by low–affinity binding of the proregion" *J. Biol. Chem.,* 269:22007–22013 (1994).

Wisniewski et al., "Apolipoprotein E: binding to soluble alzheimer's β–amyloid" *Biochem. Biphys. Res. Commun.,* 192:359–365 (1993).

Yankner et al., "Neurotrophic and neurotoxic effects of amyloid β protein: reversal by tachykinin neuropeptides" *Science* 250:279–282 (1990).

Young et al., "Amylin and syndrome–X" *Drug Development Research,* 32:90–99 (1994).

Zhu et al., *Nature* 339:483–484 (1989).

Ellis et al, "The molecular chaperone concept" *Biochem. Soc. Symp.* 55:145–153.

Fraser et al., "Biochemistry of alzheimer's disease amyloid plaques" *Clin Biochem.,* 26:339–349 (1993).

Friguet et al., "A convenient enzyme–linked immunosorbent assay for testing whether monoclonal antibodies . . . " *J. of Immuno. Methods,* 60:351–358 (1983).

Mendoza et al., "Chaperonin cpn60 from *Escherichia coli* protects the mitochondrial enzyme rhodanese . . . " *J. Bio. Chem.,* vol. 265, No. 25:17631–17634 (1992).

Shinde et al., "Folding pathway mediated by an intramolecular chaperone" *Proc. Natl. Acad. Sci. USA,* 90:6924–6928 (Aug., 1993).

Wisniewski and Frangione, "Apolipoprotein E: a pathological chaperone protein in patients with cerebral and systemic amyloid" *Neuroscience Letters,* 135:235–238 (1992).

Vallee, "Active center of carboxypeptidase A" *Federation Proceedings,* vol. 23, Part I, Jan.–Feb. (1964).

PREVENTION OF PROTEIN AGGREGATION

TECHNICAL FIELD

The present invention relates to the use of monoclonal antibodies, genetically engineered antibody fragments and small peptides which mimic antigen binding sites on the antibody for the prevention of protein aggregation in vivo and in vitro.

BACKGROUND OF THE INVENTION

When proteins are synthesized they generally must fold and assemble into a three dimensional form to be active. Initially, it was thought that proper folding was inherent in the amino acid sequence. Recent work has shown that additional proteins, now referred to as molecular chaperones, are required to mediate the folding process or unregulated aggregation of the polypeptides will occur preventing the formation of functional proteins (Goloubinoff et al., 1989; Welch, 1993). However, despite the existence of chaperones, aggregation of protein still occurs in vivo and can contribute to, or cause, various disease states.

Other factors must contribute to the occurrence of aggregation. These factors can include mutations of naturally occurring chaperones inhibiting function or allowing function with low efficiency (Wetzel, 1994). Further, "pathological", chaperones have been found which have been defined as "a group of unrelated proteins that induce beta-pleated conformation in amyloidogenic polypeptides" (Wisniewski and Frangione, 1992). It would be useful to be able to replace or augment the activity of the chaperones where necessary and to counteract the activity of pathological chaperones when present.

Protein aggregation is of major importance in biotechnology for the in vitro production of recombinant proteins. In vitro aggregation limits the protein stability, solubility and yields in production of recombinant proteins. In cells during production of recombinant proteins, aggregation is a major impediment of recombinant proteins leading to formation of inclusion bodies in the host cells (DeYoung et al, 1993; Wetzel, 1994; Vandenbroeck et al., 1993).

Further, in vivo protein aggregation or precipitation is the cause, or an associated pathological symptom, in amyloid diseases such as Down's syndrome, Alzheimer's disease, diabetes and/or cataracts, and in other disorders (DeYoung et al., 1993; Haass and Selkoe, 1993; Wetzel, 1994).

Several peptides including β-amyloid, have been shown to spontaneously self-associate, or aggregate, into linear, unbranched fibrils in serum or in isotonic saline (Banks and Kastin, 1992; Haass and Selkoe, 1993). At least fifteen different polypeptides are known to be capable of causing in vivo different forms of amyloidosis via their deposition in particular organs or tissues as insoluble protein fibrils. Iron, zinc, chromium or aluminum can participate in this aggregation (Bush et al., 1994).

Molecular chaperones were initially recognized as stress proteins produced in cells requiring repair. In particular, studies of heat shock on enzymes led the way to the discovery of molecular chaperones that function not only during cellular stress but normally to produce properly folded proteins. The heat shock model is still one of the models of choice in studying molecular chaperones (Welch, 1993; Goloubinoff et al., 1989).

Molecular chaperones are a ubiquitous family of proteins that mediate the post-translational folding and assembly of other unrelated proteins into oligomeric structures. They are further defined as molecules whose functions are to prevent the formation of incorrect structures and to disrupt any that form. The chaperones non-covalently bind to the interactive surface of the protein. This binding is reversed under circumstances that favor the formation of the correct structure by folding. Chaperones have not been shown to be specific for only one protein but rather act on families of proteins which have the same stoichiometric requirements, i.e specific domains are recognized by chaperones. This does not provide the specificity required for therapeutic activity.

Further uses and descriptions of molecular chaperones are set forth in PCT published international patent application 93/11248, 93/13200, 94/08012 and 94/11513 incorporated herein by reference and in particular 94/08012 page 2 line 20 through page 5, line 14.

PCT published international patent application 93/11248 discloses the use of a chaperone in cell culture to promote efficient production of protein in transformed cells by co-expression of the chaperone molecule. This disclosure does not provide specificity as to which proteins are protected except through co-expression with the wanted protein nor does it provide information on how to use chaperones therapeutically.

PCT published international patent application 93/13200 discloses the use of a chaperone in a purification step for a recombinant protein isolated from a cell culture and also a fusion protein of the chaperone and recombinant protein. This disclosure also does not provide specificity as to which proteins are protected except through co-expression with the wanted protein nor does it provide information on how to use chaperones therapeutically.

PCT published international patent application 94/08012 discloses the use of a chaperone in cell culture to promote increased secretion of an overexpressed gene product in a host cell. This disclosure does not provide specificity as to which proteins are protected except through co-expression with the wanted protein nor does it provide information on how to use chaperones therapeutically.

PCT published international patent application 94/11513 discloses the use of a vector containing a molecular chaperone for treating neoplasms. This disclosure does not provide specificity as to which proteins are protected except through co-expression with the wanted protein nor does it provide information on how to use chaperones therapeutically to treat diseases or syndromes which involve protein aggregation.

In each of the aforementioned publications, the chaperones did not bind to native proteins and did not redissolve aggregated proteins.

Recent reports suggest that monoclonal antibodies (mAb) can have chaperone-like activity. The feasibility of using monoclonal antibodies to assist in the in vitro refolding process of guanidine-denatured S-protein was reported recently (Carlson and Yarmush, 1992). Previously, Blond and Goldberg (1987) used monoclonal antibodies as a tool in the identification and characterization of folding steps that involve the appearance of local native-like structures in $B_2$ subunit of tryptophansynthase. Since the mAb is epitope specific, the use of mAb provides more specificity than molecular chaperones. mAbs can be sought and engineered (Haber, 1992) that bind to the particular epitope in the protein of interest that is involved in the folding process.

The main difference between mAbs and molecular chaperones is that the latter does not bind to native proteins and is capable of interacting with many different polypeptide chains without exhibiting an apparent sequence preference (Goloubinof et al., 1989). Moreover, chaperones suppress aggregation but do not redissolve aggregate already present. Similar behavior was recently reported for α-crystalin which, similar to other chaperones, does not react with active proteins, but forms a stable complex with denaturing or partially unfolded proteins, stabilizing against further aggregation (Rao et al., 1994).

Aggregated amyloid β-protein (βA4) is a major constituent of the abnormal extracellular amyloid plaque that characterizes the brains of victims of Alzheimer's disease (AD) (Haass and Selkoe, 1993). In vitro studies have shown that some of the metal ions found in biological systems, i.e. Fe, Al and Zn, can accelerate the aggregation process dramatically. The presence of "pathological" chaperones (Wisniewski and Frangione, 1992) and the above listed metals (Mantyh et al., 1993; Fraser et al., 1993) as proposed risk factors in Alzheimer's disease, favor β-amyloid cascade aggregation. If the interaction between the metal ion and the β-amyloid can be interrupted or prevented, then metal-induced aggregation can be reduced or eliminated. However, just binding a mAb at this site might prevent the metal-induced aggregation but would not allow normal functioning of the protein.

It would therefore be useful to develop the appropriate mAb with chaperone-like characteristics directed to the appropriate epitope on the β-amyloid molecule in order to prevent the accelerated metal-induced aggregation.

Further, it would be particularly useful to be able to develop a mAb as needed that prevents the aggregation of enzymes in vivo but that still allows the enzymes to function.

Still further, it is not always possible to isolate the appropriate chaperone for preventing aggregation of a molecule and to utilize it as a therapeutic. The availability of engineering and selecting mAbs and delivery systems for mAb makes it useful to develop specific mAb to serve as therapeutic chaperones.

SUMMARY OF THE INVENTION AND ADVANTAGES

According to the present invention, a method is provided of selecting anti-aggregation molecule such as a monoclonal antibody, a genetically engineered antibody fragment or a peptide which mimics the binding site of an antibody. These anti-aggregation molecules are able to bind to a native target molecule epitope with a high binding constant and must be non-inhibitory to biological activity of the target molecule.

The present invention further provides a method of treating a protein aggregation disease by creating an expression vector comprising nucleic acid including a sequence which encodes in expressible form the human form of the anti-aggregation molecule that binds to a native target molecule, an aggregating protein, and which prevents aggregation and allows biological activity of the target molecule.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
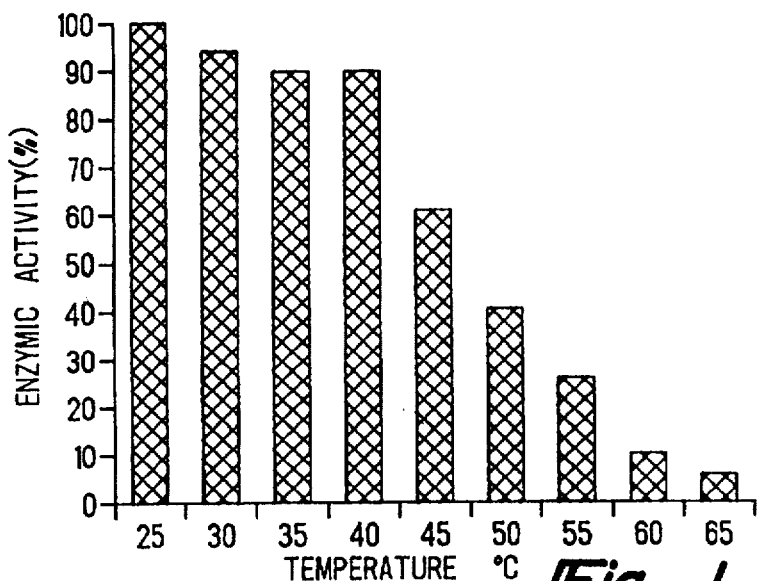
FIG. 1 is a bar graph of the temperature-dependence of enzymic activity of Carboxypeptidase A; the residual enzymic activity of CPA after one hour incubation at increasing temperatures was measured using esterase substrate.

The present invention provides a method of selecting monoclonal antibodies, genetically engineered antibody fragments and small peptides which mimic binding sites of the antibodies and which prevent aggregation and yet do not inhibit bioactivity. These anti-aggregation molecules with chaperone-like activity are able to bind to a native target molecule epitope with a high binding constant and must be non-inhibitory to the biological activity of the target molecule. The method includes culturing an appropriate host cell transformed with DNA encoding the target molecule. The host cell chosen will express the target molecule in aggregated form. Examples of such cells are set forth in PCT published international patent application 93/11248, 93/13200 and 94/08012. Alternatively, the appropriate recombinant target molecule can be purchased or a naturally occurring molecule can be isolated or purchased.

The expressed target molecule is recovered and denatured. The denatured target molecule is mixed with the presumptive anti-aggregation molecule such as a monoclonal antibody, genetically engineered antibody fragment or small peptide which mimics an antibody binding site generally as set forth in PCT pending application 93/13200 and under conditions which allow for self-aggregation, temperature, pH or interaction with other aggregation-inducing agents. It is then determined if the mixture produces nonaggregated target molecules that are bioactive even in the presence of, and bound to, the presumptive anti-aggregation molecule.

In addition, the anti-aggregation molecule is screened for its ability to dissolve already aggregated proteins. The aggregated proteins are mixed with the anti-aggregation molecules under physiological conditions. It is then determined if the mixture produces nonaggregated target molecules that are bioactive even in the presence of, and bound to, the presumptive anti-aggregation molecule.

The antibodies, or peptide mimicking the binding site, must bind to an epitope on the target molecule which is a region responsible for folding or aggregation. In addition the anti-aggregation molecule is selected only if it does not show immune cross reactivity with other proteins with proximity to the target molecules under the same conditions employed in the bioactivity tests; that is, molecules which are found in the cell near the target molecule or molecules with sequences similar to the target molecules.

After the identification of the anti-aggregation molecules has been completed, it is possible to utilize two or more to prevent or reverse aggregation. They can be used concurrently to increase their chaperone-like effect, if their respective target epitopes are not overlapping and if, in binding to the target molecule, they do not interfere with each other.

Bioactivity is tested as is appropriate for the target molecule. For example, enzymatic activity of the target molecule for its substrate can be measured. Assays which measure in vitro enzymatic bioactivity are well known to those skilled in the art.

In the preferred embodiment of the method, the target molecule is β-amyloid and the monoclonal antibody is an anti-β-amyloid monoclonal. Alternatively, a genetically engineered antibody fragment as described hereinbelow can be used or a small peptide which mimics the antigen binding site of the antibody. The antigen binding site of an antibody can be determined from the DNA sequence of the respective CDR fragments.

The method has also been demonstrated with carboxypeptidase A as set forth in the Examples hereinbelow.

Other peptides or proteins with evidence of self aggregation can also be used in the present invention such as amylin (Young et al., 1994); bombesin, caerulein, cholecystokinin octapeptide, eledoisin, gastrin-related pentapeptide, gastrin tetrapeptide, somatostatin (reduced), substance P; and peptide, luteinizing hormone releasing hormone, somatostatin N-Tyr (Banks and Kastin, 1992).

Once an appropriate monoclonal antibody with chaperone-like activity is found or engineered or a peptide with the appropriate configuration, the present invention provides for its use therapeutically to prevent or reduce protein aggregation in vivo. In the preferred embodiment, the prevention of β-amyloid aggregation is undertaken.

A method of treating a protein aggregation disease intracellularly includes the steps of preparing (Haber, 1992; Harlow & Lane, 1988) or selecting an anti-aggregation molecule, such as a monoclonal antibody, genetically engineered monoclonal antibody fragment or peptide that mimics the binding site of an antibody, that binds to an aggregating protein which is the cause of a disease and which prevents aggregation and yet allows the protein to be bioactive. This molecule can be referred to as an anti-aggregation molecule with chaperone-like activity. An expression vector is created comprising nucleic acid including a sequence which encodes in expressible form the anti-aggregation molecule. The expression vector is then delivered to the patient.

In the preferred embodiment the human monoclonal antibody that binds to an aggregating protein and which prevents aggregation is utilized. In a further preferred embodiment the monoclonal antibody is an anti-β-amyloid and is designated AMY-33 which recognizes amino acids 1–28 of β-amyloid.

Work by Dueñas et al. (1994) and Marasco et al. (1993) have shown that single chain monoclonal antibodies are efficient for intracellular expression in eukaryotic cells. The single chain monoclonal antibody is composed of an immunoglobulin heavy chain leader sequence and heavy and light chain variable regions that are joined by an interchain linker. Marasco et al. (1993) have shown that such antibodies are not toxic to the cells and function when expressed in the cell.

The production of expression vectors is well known to those skilled in the art. In a preferred embodiment, the expression vector is constructed using the methodology as set forth by Dueñas et al. (1994), PCT pending application 94/11513. Methods not explicitly set forth are performed as generally set forth in Sambrook et al., Molecular Cloning: A Laboratory Manual, Cold Springs Harbor Laboratory, New York (1992), and in Ausubel et al., Current Protocols in Molecular Biology, John Wiley and Sons, Baltimore, Md. (1989).

Such vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The expression vector can be a virus. Further the virus can be an RNA virus such as a disabled retro virus or a retrovital shuttle vector. The expression vector can also be vaccinia virus or an adenovirus. The expression vector can also be a plasmid. In a preferred embodiment wherein β-amyloid in the targeted molecule the expression vector is selected that is known to target the central nervous system.

In the present invention, the expression vector for use as a therapeutic agent comprises a nucleic acid including at least one sequence which encodes in expressible form an anti-aggregation molecule, which molecule binds to an aggregating protein that is the cause of a disease and which prevents aggregation but does not interfere with bioactivity. In a preferred embodiment the expression vector includes the sequence for a human monoclonal antibody that is an anti-β-amyloid monoclonal antibody with heparan-like characteristics. In a further preferred embodiment, the expression vector includes the sequence for the single chain monoclonal antibody of the above anti-β-amyloid mAb.

A specific example of DNA vital vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus such as antibiotic sensitivity. Negative selection is therefore a means by which infection can be controlled because it provides inducible suicide through the addition of antibiotic. Such protection ensures that if, for example, mutations arise that produce altered forms of the vital vector or recombinant sequence, cellular transformation will not occur. Features that limit expression to particular cell types can also be included. Such features include, for example, promoter and regulatory elements that are specific for the desired cell type.

In addition, recombinant vital vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original vital particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of vital vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a vital vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new vital particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The expression vector containing the sequence for the anti-aggregation molecule may be administered to mammals, including humans, by any route appropriate to the condition being treated and in several ways. Suitable routes include oral, rectal, nasal, topical, vaginal and parenteral. It will be appreciated that the preferred route may vary with, for example, the condition of the recipient and the type of treatment envisaged.

If vital vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection. Alternatively, the method as set forth by Tuomanen et al. (1993) can be used.

The vectors can be introduced into cells or tissues by any one of a variety of known methods within the art. Such methods can be found described in Sambrook et al. and Ausubel et al., and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

An alternate mode of administration of the vector can be by direct inoculation locally at the site of the disease or pathological condition or by inoculation into the vascular system supplying the site with nutrients. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

The expression vector of the present invention may be administered to the patient alone or in combination with liposomes or other delivery molecules. The expression vector is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art. The amount must be effective to achieve in the treated patients a reduction in protein aggregation and may also include but is not limited to improved survival rate, more rapid recovery, or improvement or elimination of symptoms and are selected as appropriate measures by those skilled in the art.

While it is possible for the expression vector to be administered alone, it is preferable to present it as a pharmaceutical formulation. The formulations of the present invention comprise at least one active ingredient: the monoclonal antibody or expression vector together with one or more pharmaceutically acceptable carriers and optionally other therapeutic ingredients. The carrier(s) must be acceptable in the sense of being compatible with the other ingredients of the formulation and not deleterious to the recipients. The carriers must also be selected so as not to interfere with the activity of the active ingredient.

The availability of monoclonal antibodies which bind to a specific antigen at distinct and well defined sites has led to a better understanding of the effects of highly specific enzyme-antibody interactions on the enzyme behavior. By appropriate selection it has been possible to isolate those antibodies that are non-inhibitory to biological activity of the enzyme and bind at "strategic locations" on the antigen molecule, resulting in a considerable stabilization effect of the enzyme conformation. Moreover, such monoclonal antibodies, when properly selected, prove to have a chaperone-like activity leading to a considerable refolding effect on the enzyme which was already partially heat denatured. In addition, the use of engineered monoclonal antibodies and their fragments, as well as peptides which mimic the binding site for the antigen on the antibody can be used in the present invention.

Carboxypeptidase A shows a decrease in solubility with an increase in temperature, accompanied by loss of enzymic activity and conformational changes leading to its aggregation. In the present study, the suppression of enzyme aggregation via its interaction with two monoclonal antibodies raised against native protein was investigated. ELISA measurements and determination of residual enzymic activity, as a probe of the native structure, were used to monitor the protein aggregation process. The studied monoclonal antibodies are non-inhibitory to the biological activity of the antigen or target molecule, bind on the strategic position on the molecule and proved to have a chaperone-like activity in the prevention of protein aggregation. The antibodies effect on the inhibition of aggregation was found to be related to the location of the antigenic site of each antibody. Based on the experimental data, the formation of the immunocomplexes will provide a general and convenient method for suppression of aggregation and stabilization of the target molecules without affecting the biological properties of the given target molecule. The present invention uses genetically engineered antibodies obtained from such selected antibodies as protecting agents of in vivo aggregation of their antigen, leading to production of a soluble and stabilized protein.

Protein aggregation is of major importance that extends into mechanisms of human diseases and fundamental aspects of protein folding, expression and function. Data in literature (De Young et al., 1993; Wetzel, 1994; Wetzel, 1991) suggests that aggregation is non-specific in the sense that addition of other proteins can influence the extent of aggregation of a certain protein. However, the specificity can be related to a particular residue or group of residues which play a special role in the folding-related aggregation of a polypeptide (Silen and Agard, 1989; Zhu et al. 1989; Winter et al., 1994; Brems 1988). The identification of such classes of sequences that play a role in the folding-unfolding and/or solubilization-aggregation provides the basis of the present invention for the prevention of aggregation.

Stabilization procedures based on protein-protein recognition processes, fundamental to biology, have been previously investigated (Chothia and Janin, 1975; Jaenicke, 1991). Introduction of molecular chaperones which enable folding and stabilization of unrelated proteins appears to be tailored to prevent misfolding and aggregation at an early stage during folding. However, the central problem remaining in in vivo folding is how to efficiently prevent aggregation without blocking the forward pathway of correct folding and biological activity of the native state (Ellis et al. 1991; Gething and Sambrook, 1992; Hendrick and Hartl, 1993).

The availability of monoclonal antibodies (mAbs) led to a better understanding of the effect of highly specific antigen-antibody interactions on the antigen or target molecule behavior. The complementary conformation between the interacting regions of the antibody with its antigen confers the high specificity and stability to the immunocomplex formed (Goldberg, 1991). Properly selected monoclonal antibodies, unlike the ubiquitous nature of the chaperones, bind to a specific antigen at a distinct and preselected antigenic site without interfering in the biological activity of the antigen and assist in antigen refolding (Blond and Goldberg, 1987; Carslon and Yarmush, 1992; Solomon and Schwartz, 1995).

The present invention utilized the effect of immunocomplexation in the suppression of antigen aggregation using as a model system the interaction of Carboxypeptidase A (CPA) and its monoclonal antibodies. CPA occupies a prominent position in the literature of metalloenzymes, being a well-characterized zinc exopeptidase that exhibits both peptidase and esterase activity (Vallee and Galdes, 1984). A large number of mAbs were prepared by the application towards native enzymes (Solomon et al. 1984) and their properties were widely investigated. Some of these antibodies bind to the enzyme with a relatively high binding constant, remote from its active site and assist in refolding of already heat denatured enzyme (Solomon and Schwartz, 1995). ELISA measurements and determination of residual enzymic activity as a probe of native structure are used to monitor the effect of two different mAbs, namely $CP_{10}$ and $CP_9$ on the inhibition of CPA aggregation.

The above discussion provides a factual basis for the use of monoclonal antibodies and genetically engineered antibody fragments as therapeutics for the prevention of protein aggregation. The methods used with and the utility of the present invention can be shown by the following examples.

EXAMPLES

METHODS AND REAGENTS

Carboxypeptidase A (CPA)

CPA was obtained as an aqueous crystalline suspension (Sigma Chemical Co., St. Louis, Mo.). The crystals were washed with double-distilled water, centrifuged, and dissolved in 0.05M Tris-HCl/0.5M NaCl buffer, pH 7.5. Insoluble material was removed by centrifugation. The enzyme concentration was derived from the absorbance at 278 nm.

Determination of CPA Enzymatic Activity

The enzymatic activities of CPA and its immunocomplexes were determined spectrophotometrically at 254 nm using either 1 mM hippuryl-L-phenylalanine as peptidase substrate or hippuryl-DL-$\beta$-phenyllactic acid as esterase substrate in 0.5M NaCl/0.05M Tris-Hl, pH 7.5, (Solomon et al., 1989).

Amyloid

Amyloid peptides, A$\beta$ 1–40 (Cat. No. A-5813) and A$\beta$ 1–28 (Cat. No. A-1084) corresponding to amino acids 1–40 and 1–28 of A$\beta$ respectively, were purchased from Sigma Chemical Co., St. Louis, Mo., USA).

Amyloid solutions were prepared by dissolving the peptides in water at concentration of 10 mg/ml. The stock solution was stored in aliquotes at −20° C.

Aggregating agents

Heparan sulfate (Cat. No. H 5393) was purchased from Sigma Chemical Co., St. Louis, Mo., USA). Stock solutions of metal chlorides were made up from dry salts at concentration of 1 mM in TRIS pH 7.4.

Monoclonal Antibody Production

In general, monoclonal antibodies may be prepared against a synthetic peptide based on the sequence, or prepared recombinantly by cloning techniques or the natural gene product and/or portions thereof may be isolated and used as the immunogen. Such proteins or peptides can be used to produce monoclonals by standard production technology well known to those skilled in the art as further described generally in Harlow and Lane, Antibodies: A Laboratory Manual, Cold Spring Harbor Laboratory, Cold Spring Harbor, N.Y., 1988 and Milstein (1980). Briefly, mouse monoclonal antibodies were prepared by hyperimmunization of an appropriate donor with the protein or peptide fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The harvested monoclonal antibody can be bound to a solid support substrate or conjugated with a detectable moiety or be both bound and conjugated as is well known in the art. For a general discussion of conjugation of fluorescent or enzymatic moieties see Johnstone & Thorpe, Immunochemistry in Practice, Blackwell Scientific Publications, Oxford, 1982. The binding of antibodies to a solid support substrate is also well known in the art. (see for a general discussion Harlow & Lane Antibodies: A Laboratory Manual, Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, $\beta$-galactosidase, peroxidase, urease, fluorescein, rhodamine, tritium, $^{14}$C and iodination.

Alternatively, commercially available antibodies can be used. $\alpha$-Human $\beta$-amyloid 6F/3D was obtained from ACCURATE Chemical and Scientific Corp. (Westbury, N.Y., USA). mAb AMY 33 was purchased from ZYMED San Francisco, Calif., USA. A polyclonal, affinity purified rabbit IgG obtained against the synthetic Alzheimer $\beta$-amyloid (Cat. No. 1381431) was purchased from Boehringer-Mannheim, GmbH, Germany.

Purification and characterization of anti-CPA mAbs

The monoclonal antibodies, CP-10, CP-9, which interact with CPA at high binding constants, were selected for further study. The preparation and characterization of the monoclonal antibodies $CP_{10}$ and $CP_9$ (chosen for the present study) were previously described (Solomon et al., 1989; Solomon and Balas, 1991).

These antibodies were isolated and purified by affinity chromatography on protein A-Sepharose from the corresponding ascites fluids according to Harlow and Lane.

Protocol for Determining Effect of Monoclonal Antibody Binding on CPA Activity

CPA (1 mg/ml) was incubated at 50° C. in the absence and in the presence of increasing amounts of mAbs $CP_{10}$ and $CP_9$ (100 µl in PBS) ranged between 0–2 molar ratio antibody/CPA. The enzymic activities of the immunocomplexes formed were measured as described herein above. Data related in percentage, 100% being considered the enzymic activity of CPA before denaturation.

ELISA Tests

The antigen-coating solutions (100 µl containing native CPA (10–25 µl ml) in PBS, pH 7.4, were incubated overnight at 4° C. in a polystyrene ELISA plate (Costar, Cambridge, Mass.). Diluted ascites fluid (0.1 ml) containing the desired mAb (1:2000 to 1:18.000 v/v in PBS) was added and incubated at 37° C. for 1 hour. The amount of bound mAb was determined with $\beta$-galactosidase-linked F(ab)$_2$ fragments of sheep anti-mouse IgG (Amersham International, UK).

The quantitation of the amount of aggregated CPA during denaturation at 50° C. was determined by competitive and sandwich ELISA, as follows:

Competitive ELISA Assays

CPA (10 µl/ml of PBS) was adsorbed onto ELISA plates overnight at 4° C., the remaining active groups on the plate being blocked with non-fat milk. To the soluble CPA (200 ng in 10 µl PBS), incubated for one hour at 50° C., the mAb $CP_{10}$ (molar ratio 1:1 Ab/CPA) was added and allowed to interact with the remaining soluble CPA for one hour at 37° C. In parallel, the mAb was added to the CPA solutions before exposure at 50° C. for one hour. After incubation, the CPA preparations were removed by centrifugation at 15,000 rmp for 15 minutes and applied on the ELISA plates coated with CPA. The antibody which did not bind to soluble CPA in the reaction mixture will bind to the coated CPA; the amount of antibody bound to the coated antigen will be conversely proportional to the extent of CPA aggregation and determined using $\alpha$-mouse antibodies labeled with horseradish peroxidase (HRP). The color developed by HRP (0-phenylenediamine (OPD) as substrate) was measured at $OD_{495}$ using an ELISA plate reader. The amount of antibody bound on the coated CPA in the absence of soluble CPA was considered as 100%.

Sandwich ELISA

The ELISA plates were coated with rabbit polyclonal antibodies raised against CPA (1 µl/well) by incubation at 37° C. for two hours. The residual active groups were blocked by non-fat milk. Soluble CPA (200 ng in 10 µl PBS) was exposed to 50° C. for one hour and the aggregated CPA was removed by centrifugation at 15,000 g for 15 minutes. The residual soluble CPA was incubated for another one hour at 37° C. with mAb $CP_{10}$ and mAb $CP_9$ at various molar ratio antibody/antigen. In another set of experiments, the mAbs were added to the reaction mixtures before incubation at 50° C. and then exposed for one hour at 50° C. After the incubation period, all the immunocomplexed CPA preparations were centrifuged and added to the ELISA plate, previously coated with polyclonal CPA antibodies, for 12 hours at 4° C. The amount of mAb bound, determined as described above, will be proportional to the amount of soluble CPA which remained after exposure to aggregation conditions. The results are presented in percentages, 100% being the maximal absorbance obtained before CPA heat treatment.

All data presented are the mean of triplicate determinations. The standard deviation of the intra-assay and interassays were less than 5% in all cases.

Amyloid ELISA Assays

The ELISA plates were coated with rabbit polyclonal antibodies (Boeringer-Mannheim) raised against synthetic α-amyloid (1–40) (Sigma) (100 ng/well) via covalent attachment to epoxy-coated ELISA plates by incubation at 4° C. for 16 hours. The residual epoxy groups were blocked by non-fat milk. The reaction mixtures containing aqueous solution of α-amyloid (100 ng/ml), heparan sulfate (50 mM) and/or chloride metal solutions ($10^{-3}$M at pH 6.5), were incubated at 37° C. for three hours. The aggregated β-amyloid preparations were removed by centrifugation at 15,000 g for 15 minutes. The residual soluble β-amyloid was incubated for another one hour at 37° C. with mAbs AMY 33 and/or 6F3D at equal molar ratio antibody/antigen. In another set of experiments, the mAbs were added to the reaction mixtures before incubation at 37° C. and then incubated together for 3 hours at 37° C. After the incubation period, the immunocomplexed amyloid preparations were added to the ELISA plates, previously coated with polyclonal anti-amyloid antibodies. The amount of mAb bound will be proportional to the amount of soluble amyloid which remained after exposure to aggregation conditions.

The amount of bound antibody was determined using a-mouse second antibodies labeled with horseradish peroxidase (HRP). The enzyme activity of HRP is directly proportional with the amount of residual amyloid bound to rabbit polyclonal antibodies. The enzyme activity of HRP was measured using O-phenylenediamine (OPD) as substrate. The color developed was measured at $A_{495}$ using an ELISA reader. Data represent the mean of triplicate determinations. The standard deviation of the intra-assay and interassays were less than 5% in all cases.

EXAMPLE 1

Aggregation of heat denatured CPA was followed by determination of the residual enzymic activity of CPA using esterase and peptidase substrates. CPA (1 mg/ml) was incubated at various temperatures for one hour, and residual enzymic activity was determined. The temperature of 50° C. was chosen for further study. At this temperature, mAbs studied keep all their immunological activity (personal data). Effect of immunocomplexation of CPA with its mAbs was monitored by: (1) Determination of enzymic activity and (2) ELISA measurements as described herein above.

Monoclonal antibodies raised against native antigens proved to be powerful tools in identification and characterization of folding steps by recognition of incompletely folded antigens (Mendrick and Hartl, 1993). The selected antibodies might interact at sites where protein unfolding is initiated, thereby stabilizing the protein and suppressing further aggregation.

The main difference between mAbs and molecular chaperones is that the latter does not bind to native proteins and is capable of interacting with many different polypeptide chains without exhibiting an apparent sequence preference (Goloubinof et al., 1989). Moreover, chaperones suppress aggregation but do not redissolve aggregate already present.

Figure 2:
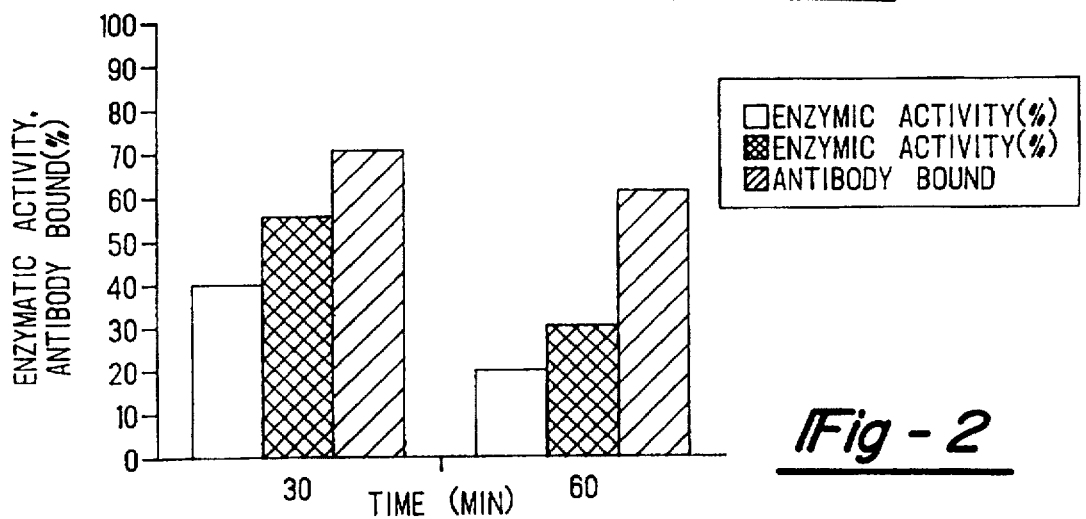
FIG. 2 is a bar graph of the time course of denaturation of Carboxypeptidase A after exposure at 50° C.; the residual esterase (single cross-hatch bars) and peptidase (open bars) enzymic activity of CPA was measured at two intervals of incubation at 50° C.; the amount of residual soluble enzyme was determined by sandwich ELIAS (bars of diagonal lines)

The aggregation of CPA and loss of its enzymic activity was found to be dependent on the temperature and the time of incubation (FIGS. 1, 2). Esterase activity seems to be more affected at higher temperature than peptidase activity, indicating that these activities follow different reaction mechanisms (FIG. 2). These data are compatible with applicant's previous results (Solomon et al., 1989; Solomon and Balas, 1991), as well as with the findings of Vallee and his collaborators (1969), who postulate that the active site of CPA consists of non-identical but interacting binding sites for peptides and ester substrates. As shown in FIG. 2, the immunological recognition of partially heat denatured enzyme is better conserved than its residual enzymic activity.

Figure 3:
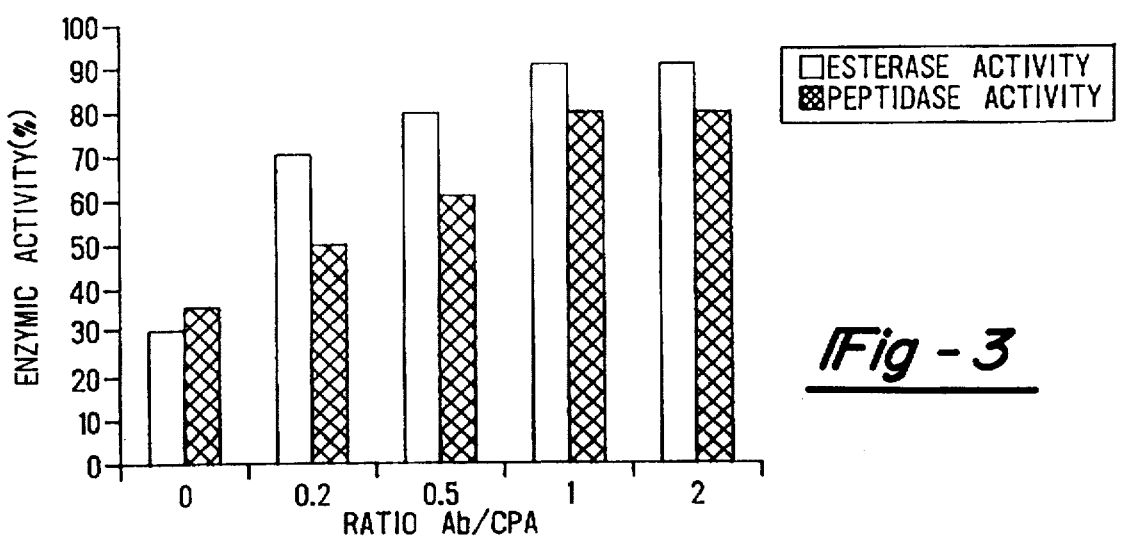
FIG. 3 is a bar graph of the enzymic activity of Carboxypeptidase A retained after exposure to 50° C. for one hour in the presence of monoclonal antibody $CP_{10}$; the immuno-complexation of CPA with increasing amounts of $CP_{10}$ was performed before exposure at 50° C. for one hour; the residual peptidase (open bars) and esterase (single cross-hatch bars) enzymic activity of CPA was measured.
Figure 4:
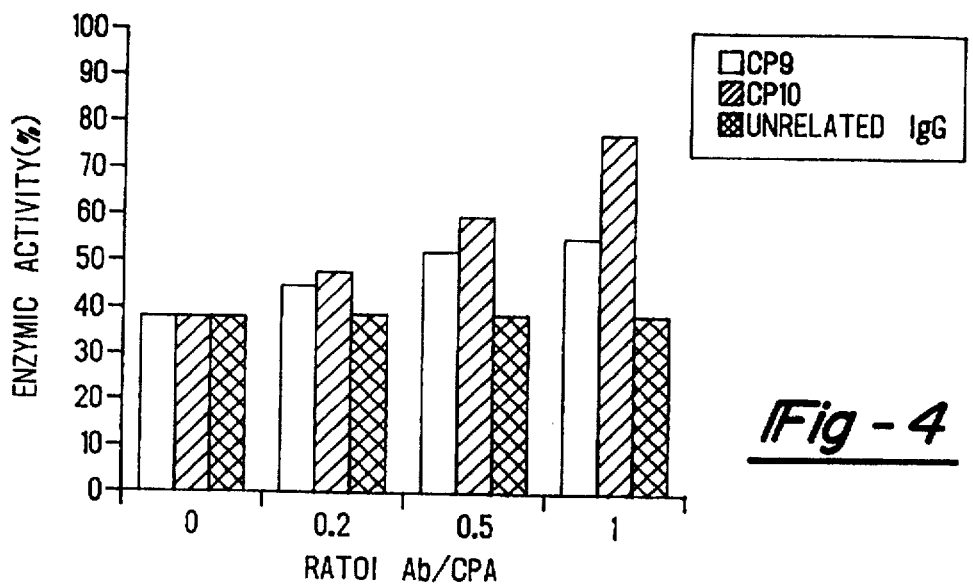
FIG. 4 is a bar graph of the effect of epitope location on the maintenance of the enzymic activity of heat-exposed Carboxypeptidase A; increasing amounts of monoclonal antibodies $CP_{10}$ (single cross-hatch bars) and $CP_9$ (diagonal lines) and unrelated IgG (bars with diagonal lines) were added to CPA before exposure to 50° C. for one hour and esterase enzymic activity was measured.

The inhibition of CPA aggregation, induced by incubation at 50° C. for one hour by its interaction with two mAbs, $CP_9$ and $CP_{10}$, was followed by measuring the peptidase and esterase enzymic activities (FIG. 3). The two mAbs, $CP_{10}$ and $CP_9$ were chosen for this study on the basis of previous data regarding their effect on the enzyme behavior (Solomon and Schwartz, 1995; Solomon et al., 1989; Solomon and Balas, 1991). The protection of enzymic activity of heated CPA was dependent on the amount of antibody added to the enzyme and a molar ratio of 1:1 antibody/enzyme was sufficient for the maximum protection effect. The peptidase activity of the CPA-$CP_{10}$ complex was maintained at 90% of its initial activity in the presence of mAb $CP_{10}$. The protective effect of mAbs on CPA activity during heat denaturation was found to be related to the location of the antigenic site of each antibody (FIG. 4). Even a great excess of unrelated antibody did not assist in maintaining CPA activity. Increase in preservation of enzyme activity can be reached, however, in the presence of a pair of two antibodies. This effect seems to be the result of a "locking" of the conformation caused by simultaneous interaction with two different antibodies at two distinct epitopes (Solomon and Balas, 1991).

Figure 5:
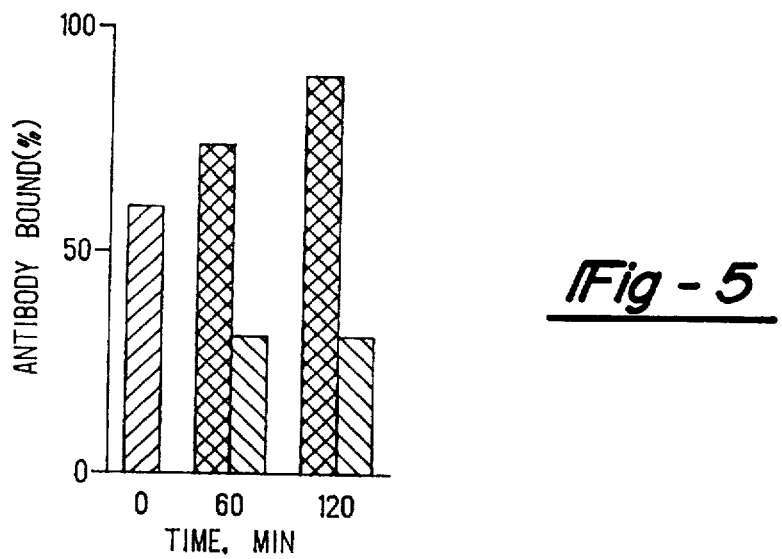
FIG. 5 is a bar graph of the prevention of aggregation of Carboxypeptidase A by monoclonal antibody $CP_{10}$; aggregation of CPA, in the presence (bars with right slanting diagonal lines) and in the absence (single cross-hatch bars) of antibodies, was followed by determination of amount of mAb bound to coated CPA in a competitive ELISA; the absorbance at 495 nm obtained in the absence of added soluble CPA was set at 100% for bound antibody; the soluble CPA, before heat exposure, competes with the coated CPA for antibody binding, leading to decrease in amount of antibody bound (60%) (bars with left slanting diagonal lines)
Figure 6:
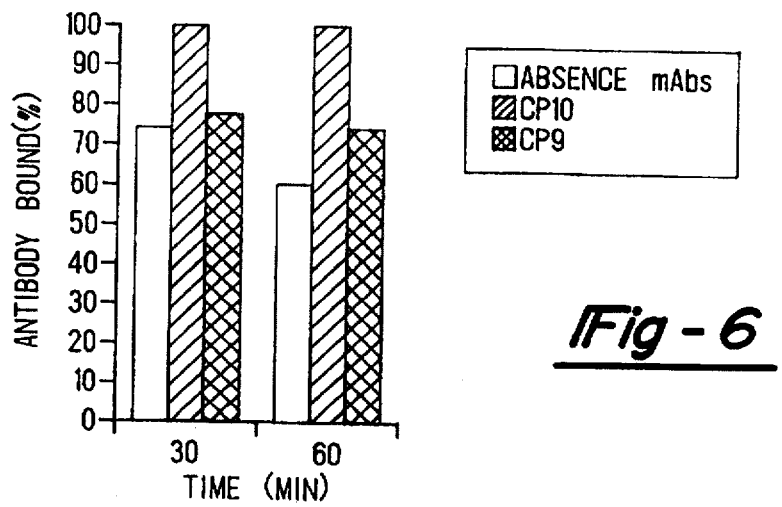
FIG. 6 is a bar graph showing thermal aggregation of Carboxypeptidase A and its suppression by monoclonal antibodies $CP_{10}$ and $CP_9$; aggregation of Carboxypeptidase A after exposure at 50° C. for one hour in the absence (open bars) of monoclonal antibodies and in the presence of $CP_{10}$ (bars with diagonal lines) and $CP_9$ (double cross-hatch) was followed by determination of amount of antibody bound by sandwich ELISA; maximum binding (100%) was considered the amount of antibody bound to CPA before exposure to aggregation conditions.

The amount of aggregated CPA was quantitated by ELISA measurements. Disappearance of CPA, as a result of its aggregation during incubation for one hour at 50° C., was followed by a competitive ELISA assay (FIG. 5) and a sandwich assay (FIG. 6). The mAb, $CP_{10}$, maintained 100% of the CPA activity in solution during heating for one hour at 50° C. (FIG. 6); $CP_9$ provided a slight effect on CPA protection at 50° C. Both antibodies prevent the aggregation of CPA, similar to the data shown in FIG. 4, recognizing "key positions" on the molecule responsible for heat denaturation and aggregation of CPA.

The biological activity of the enzyme seems to be more sensitive to high temperatures than the insolubilization process. Subtle heat-induced conformational changes occurring in CPA molecules are reflected by change in enzymic activity, even before transition between native-molten globule conformation-aggregated states occurred. These findings are in contradiction to previous suggestions that the biological function of a protein does not necessarily require fully folded protein (Hattori et al., 1993).

The antigen binding site of mAb $CP_{10}$ (previously named $CP_{10}$) was identified as one of the immunodominant regions of the enzyme, localized on the surface of the molecule between amino acids 209–218 (Solomon et al. 1989). The localization of the epitope recognized by $CP_9$ has not yet been clarified, but it does not interfere with the mAb $CP_{10}$ during simultaneous binding to CPA molecule, as suggested by additivity measurements (Solomon and Balas, 1991).

Similar effects in suppression of antigen aggregation were obtained after immunocomplexation of horseradish peroxidase.

The data available in literature suggests that for practically all the antigens it might be possible to prepare monoclonal antibodies which bind with high affinity without affecting their catalytic activity. Moreover, mAbs like the majority of immunoglobulins, are robust molecules and survive in a variety of environments, including high temperatures, low pH, denaturing agents. Formation of such immunocomplexes should provide a general and convenient method for suppression of aggregation and stabilization of their antigen without affecting the biological properties of the given antigen.

EXAMPLE 2

This example investigates the immunocomplexation effect on the in vitro aggregation of β-amyloid. Aggregation of β-amyloid was found to be dependent on the pH, peptide concentration, temperature and time of incubation (Burdick et al., 1992). In applicant's experiments, the aggregation of β-amyloid was performed by incubation of aqueous solution of βA4 (10 mg/ml) for three hours at 37° C. The β-amyloid aggregation was followed by ELISA measurements using two different commercially available monoclonal antibodies raised against β-amyloid: α-human β-amyloid 6F/3D obtained from Accurate Chemical and Scientific Corp, Westbury, N.J. USA, and mAb AMY 33 (Stern et al., 1990), purchased from Zymed, San Francisco, Calif., USA, raised against peptides 8–17 and 1–28, respectively, of the β-amyloid.

Figure 7A:
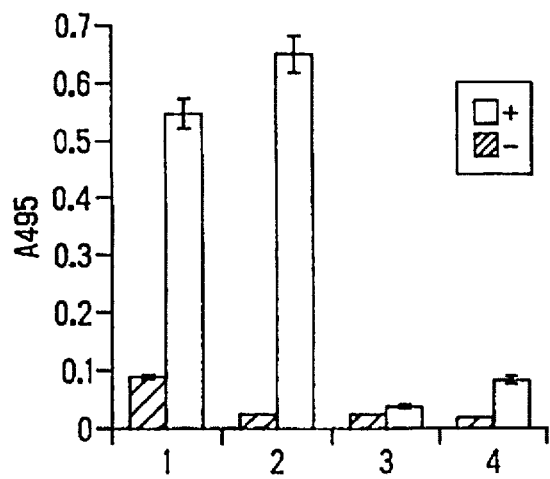
FIGS. 7A and 7B are a pair of graphs (A and B) showing aggregation of β-amyloid (1–40) in the absence (diagonal lines bars) and in the presence (open bars) of monoclonal antibodies AMY-33 (A) and 6F/3D (B) followed by ELISA; (1) β-amyloid alone, (2) β-amyloid+50 MM heparan sulfate, (3) β-amyloid+10–3M $AlCl_3$; (4) β-amyloid+$10^{-3}$M $ZnCl_2$.
Figure 7B:
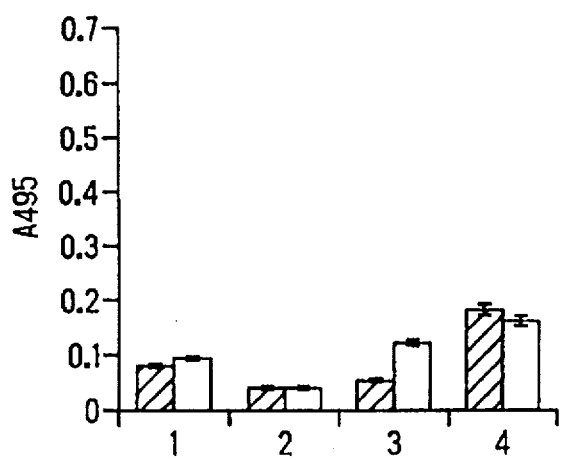

The addition of the antibodies was made before or after exposure of synthetic β-amyloid to the aggregation process (FIG. 7A, B). The aggregation of the β-amyloid was performed in the presence of heparan sulfate and/or metal ions, such as $Zn^{2+}$ and $Al^{3+}$. The antibody AMY-33, which is supposed to recognize an epitope spanned between the sequence 1–28, inhibits the β-amyloid aggregation occurring in the presence or absence of heparan sulfate (FIG. 7A). Any significant effect on metal-induced amyloid aggregation was observed under the same experimental conditions. The mAb 6F/3D, recognizing an epitope located between the sequence 8–17 of the β-amyloid, interferes with $Zn^{2+}$-induced aggregation, showing a partial solubilization effect on already aggregated β-amyloid, but has no effect on other aggregating agents (FIG. 7B).

Metals, such as $Zn^{2+}$ and $Al^{3+}$, have been proposed as risk factors for Alzheimer's disease development (Mantyh et al., 1993; Frederickson, 1989; McLachlan et al., 1991). The aggregation of βA4 induced by aluminum is distinguishable from that induced by Zn in terms of role, extent, pH and temperature dependence (Mantyh et al. 1993). Although the precise site of interaction of metal ions and βA4 is not clarified, several residues in βA4 are candidates for metal binding. The βA4 histidine residues ($His_{13}$ -$His_{14}$) may be implicated in fibril formation and it is conceivable that at least $H_{14}$ remains available for intermolecular electrostatic interactions between anti-parallel chains (Talfous et al., 1994). The site defined by $Val_{12}$-$His_{13}$-$His_{14}$-$Glu_{15}$-$Lys_{16}$-$Leu_{17}$ has been identified as a sequence containing a heparan sulfate binding domain (Fraser et al., 1992) and $His_{13}$ and $Lys_{16}$ are supposed to provide the cationic binding sites being exposed on the same face of the peptide β sheet (Talafous et al. 1994).

Figure 8:
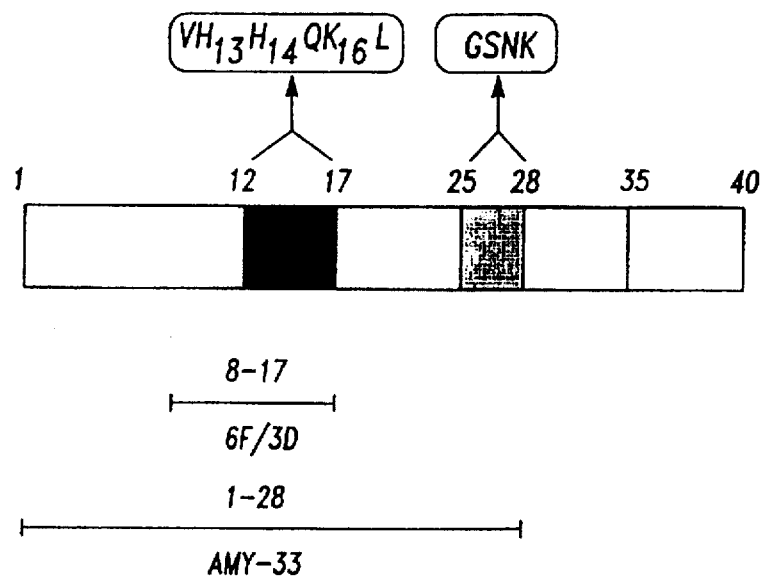
FIG. 8 shows schematic diagram of β-amyloid (1–40) with horizontal lines representing the regions against which monoclonal antibodies were produced, vertical lines and shaded rectangular areas represent the heparan sulfate binding sites (residues 12–17, dark shaded), the proposed toxic fragment (residues 25–35) and the putative epitope of mAb AMY-33 (sequence 25–28, light shaded).

Binding of mAb AMY-33 to βA4 prevents self-aggregation of the β-amyloid, probably by recognizing the sequence 25–28 located in the proposed aggregation fragment comprising the amino acids between 25–28 (Yankher et al., 1990) (FIG. 8). This antibody prevents intramolecular aggregation occurring in the presence of heparan sulfate, which is supposed to affect only the aggregation of preexisting amyloid fibers (Fraser et al., 1992). Inhibition of β-amyloid aggregation in the presence of mAb 6F/3D was partially effective only in the presence of $Zn^{2+}$.

On the basis of applicants findings regarding other antigen-antibody systems studies (Solomon et al., 1989; Solomon and Balas, 1991), the formation of the immunocomplexes with selected, highly specific monoclonal antibodies, should provide a general and convenient method to prevent aggregation of the proteins without affecting their biological properties.

At least 15 different polypeptides are known to be capable of causing in vivo different forms of amyloidosis via their deposition in particular organs or tissues as insoluble protein fibrils.

Recent advances in antibody engineering technology, as well as in the development of suitable delivery systems (Haber, 1992; Pluckthun, 1992; Travis, 1993; Marasco et al., 1993) make it possible to develop functional small antibody fragments to serve as therapeutic chaperones for the treatment of Alzheimer's disease as well as other human amyloidosis diseases by gene based therapies.

Application of the above findings for in vivo aggregation, can confer to single chain antibodies (Pluckthun, 1992) or other engineered antibody fragments, a protective role in the renaturation of recombinant proteins.

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Banks and Kastin (1992)
Blond and Goldberg, "Partly native epitopes are already present on early intermediates in the folding of tryptophan synthase." PNAS (USA), 84:1147–1151 (1987).
Brems (1988) Biochemistry 27, 4541–4545.
Burdick et al. (1992) J. Biol. Chem. 267, 546–554.
Bush et al., "Rapid Induction of Alzheimer Aβ Amyloid Formation by Zinc" Science 265:1465–1467 (1994).
Carlson and Yarmush, "Antibody assisted protein refolding." Bio/Technol., 10:86–91 (1992).
Chothia and Janin (1975) Nature 256, 705–708.

De Young et al., "Aggregation of Globular Proteins", Accounts of Chemical Research, 26:614–620 (1993).

Dueñas et al., "Intra- and Extracellular Expression of an scFv Antibody Fragment in *E. coli:* Effect of Bacterial Strains and Pathway Engineering Using GroES/L Chaperonins" BioTechniques, 16:476–483 (1994).

Ellis and Van Der Viies (1991) Annu. Rev. Biochem. 60, 321–347.

Fraser et al. (1992) J. Neurochem. 59, 1531–1540.

Frederickson (1989) Int. Rev. Neuorobiol. 31, 145–238 (1989).

Gerbing and Sambrook (1992) Nature 355, 33–45.

Goldberg (1991) Trends Biochem 16, 358–362.

Goloubinoff et al., "Reconstitution of active dimeric ribulose bisphosphate carboxylase from an unfolded state depends on two chaperonin proteins and Mg-ATP" Nature, 342:884–889 (1989).

Haass and Selkoe, "Cellular Processing of β-Amyloid Precurson Protein and the Genesis of Amyloid β-Peptide." Cell, 75:1039–1042 (1993).

Haber, "Engineered Antibodies as Pharmacological Tools", Immunological Reviews, 130:189–212 (1992).

Harlow and Lane (1988).

Hattori et al., (1993) J. Biol. Chem. 268, 22414–22419.

Hendrick and Hartl (1993) Annu. Rev. Biochem. 62, 349–384.

Jaenicke (1991) Biochemistry, 30, 3147–3161.

Mantyh et al., (1993) J. Neurochem. 61, 1171–1173.

Marasco et al., "Design, intracellular expression, and activity of a human anti-human immunodeficiency virus type 1 gp120 single-chain antibody", Proc. Natl. Acad. Sci. USA, 90:7889–7893 (August 1993).

McLachlan et al., (1991) Lancet 337, 1304–1308.

Milstein, "Monoclonal Antibodies" Scientific American, pp 56–64 (Oct., 1980).

Pluckthun (1992) Immunol. Reviews 130, 151–188.

Rao et al., (1994) J. Biol. Chem. 269, 13266–13272.

Silen and Agard, "The x-lytic protease pro-region does not require a physical linkage to activate the protease domain in vivo." Nature, 341:462–464 (1989).

Solomon et al., (1984) Molec. Immunol. 21, 1–12.

Solomon et al., "Localization of a highly immunogenic region of Carboxypeptidase A recognized by three different monoclonal antibodies and their use in the detection of subtle conformational alterations in this enzyme region." Biochemistry, 28:1235–1241 (1989).

Solomon and Balas, "Thermostabilization of Carboxypeptidase A by interaction with its monoclonal antibodies." Biotechnol. Appl. Biochem., 14:202–211 (1991).

Solomon and Schwartz, "Chaperone-like effect of monoclonal antibodies on refolding of heat denatured Carboxypeptidase A. J. Molec. Recog." (in press) (1995).

Stern et al., (1990) FEBS Lett. 264, 43–47.

Talafous et al., (1994) Biochemistry 33, 7788–7796.

Travis (1993) Science 261, 1114.

Tuomanen et al., "Reversible opening of blood-brain barrier by anti-bacterial antibodies", Proc. Natl. Acad. Sci. USA 90::7824–7828 (August 1993)

Vallee and Riordan (1969) Ann. Rev. Biochem. 38, 733–794.

Vallee and Galdes (1984) Advances in Enzymology and Related Areas of Molecular Biology, 56, 283–430.

Vandenbroeck et al., "Refolding and single-step purification of porcine interferon-γ from *Escherichia coli* inclusion bodies—Conditions for reconstitution of dimeric IFN-γ", Eur. J. Biochem., 215:481–486 (1993).

Welch, "How Cells Respond to Stress", Scientific American, pp. 56–64 (May 1993).

Wetzel (1994) Trends Biochem. 12, 193–198.

Wetzel et al., (1991) Bio/Technol. 9, 731–737.

Winter et al., (1994) J. Biol. Chem. 269, 22007–22013.

Wisniewski et al., Biochem. Biophys. Res. Commun., 192:359–365 (1993)

Yankner et al., (1990) Science 250, 279–282.

Young et al., (1994).

Zhu et al., (1989) Nature 339, 483–484.

What is claimed is:

1. A method of selecting an anti-aggregation molecule having the chaperone-like activity of anti-aggregation, wherein the anti-aggregation molecule is selected from the group consisting of a monoclonal antibody, a genetically engineered antibody antigen binding fragment, and a single chain monoclonal antibody, and wherein said anti-aggregation molecule binds to a bioactive native target polypeptide epitope with a high binding constant and is non-inhibitory to the biological activity of the target polypeptide comprising the steps of:

denaturing a target polypeptide which aggregates, mixing the target polypeptide with said anti-aggregation molecule to form a mixture, incubating the mixture under conditions allowing for aggregation, selecting non-aggregated mixtures, and testing the nonaggregated target polypeptide coupled to the anti-aggregation molecule for bioactivity thereby selecting an anti-aggregation molecule with the chaperone-like activity of anti-aggregation which when coupled to the target polypeptide maintains bioactivity.

2. The method of claim 1 further characterized by the target polypeptide being β-amyloid.

3. A method of selecting an anti-aggregation molecule having the chaperone-like activity of anti-aggregation, wherein the anti-aggregation molecule is selected from the group consisting of a monoclonal antibody, a genetically engineered antibody antigen binding fragment, and a single chain monoclonal antibody, and wherein said anti-aggregation molecule binds to a bioactive native target polypeptide epitope with a high binding constant, reverses aggregation and is non-inhibitory to the biological activity of the target polypeptide comprising the steps of:

preparing an aggregated target polypeptide, mixing the target polypeptide with said anti-aggregation molecule to form a mixture, selecting mixtures with non-aggregated target polypeptides, and testing the target polypeptide coupled to the anti-aggregation molecule for bioactivity thereby identifying an anti-aggregation molecule with the chaperone-like activity of anti-aggregation which when coupled to the target polypeptide maintains bioactivity.

4. The method of claim 3 further characterized by the target polypeptide being β-amyloid.

* * * * *